US00PP31718P2

(12) United States Plant Patent
Cain

(10) Patent No.: US PP31,718 P2
(45) Date of Patent: May 5, 2020

(54) GRAPEVINE PLANT NAMED 'IFG FORTY-THREE'

(50) Latin Name: ***Vitis interspecific* hybrid**
Varietal Denomination: IFG Forty-three

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 16/501,434

(22) Filed: Apr. 16, 2019

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 5/0812
See application file for complete search history.

*Primary Examiner* — Kent L Bell

(57) ABSTRACT

This invention is a new and distinct grapevine variety denominated 'IFG Forty-three'. The new grapevine is characterized by producing medium size obtuse ovate shaped berries having medium firm texture, and which ripen very early in the season. Berries resist flesh browning and bruising. Berries are borne on medium size clusters which are naturally loose and do not require gibberellin applications to thin clusters.

1 Drawing Sheet

Latin name of the genus and species claimed: *Vitis interspecific* hybrid.

Variety denomination: 'IFG FORTY-THREE'.

BACKGROUND OF THE INVENTION

The new and distinct Grapevine plant described and claimed herein originated from a hand pollinated cross of cross of '04141-020-125' (unnamed *Vitis vinifera* selection from the IFG breeding program and '07130-045-183' (an unnamed interspecific hybrid from the IFG breeding program) hybridized May 2011. The abortive seed traces were subsequently embryo cultured and the resulting 141 seedlings were planted in the field in April 2012. The present variety of grapevine was selected as a single plant in July 2013 and was first asexually propagated by hardwood cuttings in December 2013 near Delano, Kern County, Calif. These resulting cuttings produced second generation plants that were planted during April 2014 near Delano, Kern County, Calif. and were observed for four years and found to reproduce true-to-type.

BRIEF SUMMARY OF THE INVENTION

The new grapevine 'IFG Forty-three' is characterized by producing medium size obtuse ovate shaped berries having medium firm texture, and which ripen very early in the season. Berries resist flesh browning and bruising. Berries are borne on medium size clusters which are naturally loose and do not require gibberellin applications to thin clusters. Berry size can be increased by applying gibberellic acid. Berries store well and can be maintained in good condition for up to 8 weeks in cold storage.

To the inventor's knowledge, the known variety to which the new grapevine variety is most similar is the 'Prime' (IL 1467). 'IFG Forty-three' differs from the 'Prime' by having much smaller residual seed traces and more uniform berry size and by being spur fruitful. 'IFG Forty-three' is also somewhat similar to the 'Sugraone' (U.S. Plant Pat. No. 3,106) (expired). It differs from the 'Sugraone' by ripening approximately seven to ten days earlier, having smaller berries and residual seed traces, and by having more uniform berry size. The basal buds of 'IFG Forty-three' are fruitful so it can be pruned to short spurs while the basal buds of 'Sugraone' are not fruitful so it has to be pruned to canes having up to fifteen buds.

'IFG Forty-three' differs from its maternal parent the 'IFG 04141-020-125' (un-named seedling selection in the IFG breeding program) by having berries that are less variable in berry size, less prone to ambering and flesh browning and by having better eating quality and by being less prone to heat damage. 'IFG Forty-three' differs from its paternal parent, 'IFG 07130-045-183' (un-named interspecific hybrid seedling selection in the IFG breeding program), by ripening earlier, by being less prone to berry browning and ambering and by exhibiting better storage ability.

BRIEF DESCRIPTION OF THE DRAWING

The accompanying photographic drawing illustrates in full color 'IFG Forty-three'. The photograph was taken outdoors with indirect lighting. The colors are as nearly true as is reasonably possible in a color representation of this type.

The left side of the drawing has a mature leaf.

A mature fruit cluster is represented in the center of the drawing along with a typical berry in cross section.

A young shoot tip can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2016 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Forty-three' plants grown in the vicinity of Delano, Kern County, Calif. during 2017 and 2018, and is believed to apply to plants of the variety grown under similar conditions of soil and climate elsewhere:

VINE

General:

*Vigor*.—Moderate to strongly vigorous.
*Density of foliage*.—Medium.
*Productivity*.—Productive, producing about 10.5 to 15.8 kg of fruit per vine.
*Root stock*.—Own root.
*Training method*.—Typically spur pruned leaving 2 bud spurs.

Trunk:

*Trunk diameter of* 4-*year-old vines at* 30 *cm above the soil line*.—Approximately 4.9 cm.
*Shape*.—Stocky.
*Straps*.—Very long, continuous.
*Surface texture*.—Shaggy texture.
*Inner bark color*.—The following colors were observed: Greyed-orange: 165A and 165B.
*Outer bark color*.—The following colors were observed: Grey: 201A and 201B and 201C.

SHOOTS

Young shoot:

*Form of tip*.—Wide open.
*Distribution of anthocyanin coloration of tip*.—Absent.
*Intensity and color of anthocyanin coloration of tip*.—Very weak on edges of immature leaf tips: Greyed-red: 180A.
*Density of prostrate hairs of tip*.—Very sparse to sparse.
*Density of erect hairs on tip*.—Absent.
*Color*.—Yellow-green: 144B.

Woody shoot (mature canes):

*Internode length*.—Medium: About 10.3 cm.
*Width at node*.—About 12.0 mm.
*Cross section*.—Circular.
*Surface*.—Smooth.
*Main color*.—The following colors were observed: Greyed-orange: 165A and 165B and 165C and 165D.
*Density of erect hairs on nodes*.—None or very sparse.
*Density of erect hairs on internodes*.—None or very sparse.
*Axillary shoot vigor at full bloom*.—Medium to weak.

Flowering shoot:

*Vigor during flowering*.—Moderate.
*Attitude during flowering on shoots not tied*.—Semi-erect.
*Color*.—Dorsal side of internodes — Yellow-green: 144A.
*Color*.—Ventral side of internodes — Yellow-green: 144A.
*Color*.—Dorsal side of nodes — Yellow-green: 144A.
*Color*.—Ventral side of nodes — Yellow-green: 144A.
*Density of prostrate hairs on nodes*.—None to very sparse.
*Density of erect hairs on nodes*.—Sparse.
*Density of prostrate hairs on internode*.—Sparse to medium dense.
*Density of erect hairs on internode*.—Sparse to medium dense.
*Anthocyanin coloration of buds*.—Absent.

Tendrils:

*Distribution on the shoot* (*at full flowering*).—Discontinuous.
*Color*.—The following colors were observed: Yellow-green: 144A.
*Form*.—Trifurcated.
*Number of consecutive tendrils*.—2.

LEAVES

Young leaves:

*Color of upper surface of first four distal unfolded leaves*.—Yellow-green: 144A.
*Color of lower surface of young leaves*.—Yellow-green: 146C.
*Average intensity of anthocyanin coloration of six distal leaves prior to flowering*.—Absent.
*Density of prostrate hairs between veins* (*lower surface*).—Sparse.
*Density of prostrate hairs on veins* (*lower surface*).—Sparse.
*Density of erect hairs between veins* (*lower surface*).—Sparse to medium.
*Density of erect hairs on veins* (*lower surface*).—Sparse to medium.

Mature leaves (opposite first cluster):

*Average length*.—About 14.6 cm.
*Average width*.—About 13.2 cm.
*Mature leaf size*.—Medium large.
*Shape of blade*.—Wedge-shaped.
*Number of lobes*.—5.
*Blade venation*.—Palmate.
*Anthocyanin coloration of main veins on upper side of blade*.—Absent.
*Mature leaf profile*.—Undulate.
*Blistering surface of blade upper surface*.—Weak.
*Leaf blade tip*.—In the plane of the leaf.
*Leaf apex*.—Broadly acute.
*Leaf margin*.—Serrate.
*Undulation of margin*.—Slight.
*Undulation of blade between main and lateral veins*.—Slight undulation over entire area.
*Shape of teeth*.—Mixture of both sides straight and both sides convex.
*Length of teeth*.—Medium.
*Ratio length/width of teeth*.—Medium.
*Shape of upper lateral sinuses*.—Closed to lobes slightly overlapping.
*Depth of upper lateral sinuses*.—Medium.
*General shape petiole sinus*.—Wide open.
*Shape of base of upper leaf sinuses*.—U-shaped.
*Tooth at petiole sinus*.—Absent.
*Density of prostrate hairs between veins on lower surface of blade*.—Sparse.

*Density of erect hairs between veins on lower surface of blade*.—Absent.
*Density of prostrate hairs on main veins on lower surface of blade*.—None or very sparse.
*Density of erect hairs on main veins on lower surface of blade*.—Very sparse.
*Density of prostrate hairs on main veins on upper surface of blade*.—Very sparse.
*Density of erect hairs on main veins on upper surface of blade*.—None.
*Autumn coloration of leaves*.—Greyed-yellow: 162A.

Upper surface:
*Color*.—The following colors were observed: Green: 137A and 137B.
*Anthocyanin coloration of main veins* (*lower surface*) .—Absent.
*Color of main veins*.—Yellow-green: 145A.
*Surface appearance*.—Semi-glossy to dull.
*Blistering surface of blade*.—Weak.

Lower surface:
*Color*.—Yellow-green: 146B.
*Coloration and intensity of anthocyanin on main veins* (*lower surface*).—Weak: Red-purple: 57B.
*Color of main veins*.—Yellow-green: 145B.
*Glossiness*.—Weak.
*Surface texture*.—Rugose.
*Surface appearance*.—Dull.

Petiole:
*Length*.—About 12.3 cm.
*Diameter of petiole 2 cm from blade*.—About 2.4 mm.
*Petiole color*.—The following colors were observed: Yellow-green: 145C and Red-purple: 57B.
*Length of petiole compared to middle vein*.—Slightly shorter.
*Density of prostrate hairs on petiole*.—None or very sparse.
*Density of erect hairs on petiole*.—None.

Buds:
*Bud fruitfulness*.—Basal: mostly fruitful.
*Position of first fruitful shoot on previous season cane*.—$1^{st}$ to $2^{nd}$ node.
*Dormant bud length*.—About 4.9 mm.
*Dormant bud width in the proximal/distal plane*.—About 4.1 mm.
*Dormant bud color*.—Greyed-orange: 165A.
*Time of bud burst*.—Early: About Mar. 13, 2018.

FLOWERS

General:
*Flower sex*.—Hermaphrodite.
*Length of single flower, unopened*.—About 3.1 mm.
*Width of single flower*.—Unopened: About 1.9 mm. Opened: About 7.4 mm.
*Stamen length*.—About 3.4 mm.
*Stamen count*.—Mixture of 4, 5 or occasionally 6 stamens per flower.
*Pollen color*.—Yellow: 10B.
*Pistil length*.—About 3.2 mm.
*Pistil color*.—Yellow-green: 144A.
*Position of first flowering and fruiting node*.—Between the $3^{rd}$ and $5^{th}$ node (current season growth).
*Number of inflorescence per flowering shoot*.—1.1 to 2: About 1.9.
*Time of bloom*.—Medium as compared with similar varieties in the growing area of Delano, Calif.
*Date of full bloom*.—About May 7, 2018.

FRUIT

General:
*Ripening period*.—Very Early: Approximately Jul. 12, 2018.
*Use*.—Fresh market.
*Keeping quality*.—Good, remains commercially acceptable when stored up to 8 weeks at 0° C. and high relative humidity.
*Resistance to*.—Insects: Average typical of *Vitis vinifera* species. Diseases: Average typical of *Vitis vinifera* species.
*Refractometer test*.—Soluble solids: About 20.0 Brix.
*Brix/acid*.—About 76.9%.
*% Titratable acidity*.—About 0.26.
*Juice pH*.—About 3.96.
*Juice color*.—Greyed-yellow: 160C.

Cluster:
*Mature cluster length* (*peduncle excluded*).—About 23.3 cm.
*Mature cluster width*.—About 11.1 cm.
*Mature cluster weight*.—About 350 g.
*Bunch density*.—Loose: single berries and some pedicels visible, berries are readily movable.
*Number of berries*.—About 71.
*Form*.—Conical.

Peduncle:
*Lignification of peduncle*.—Weak.
*Diameter of peduncle*.—Approximately 5.0 mm.
*Length of peduncle*.—Short: Approximately 4.1 cm.
*Color of peduncle*.—The following colors were observed: Yellow-green: 144A and 144B.

Berry:
*Uniformity of size*.—Uniform.
*Single berry weight*.—About 5.1 g natural; to about 5.6 g when treated with gibberellic acid.
*Shape*.—Obtuse ovoid.
*Seeds*.—Contains small rudimentary seed traces.
*Cross section*.—Circular.
*Berry dimensions*.—Longitudinal axis: About 2.5 cm. Horizontal axis: About 1.8 cm.
*Pedicel length*.—About 10.1 mm.
*Pedicel width*.—About 1.1 mm.
*Pedicel color*.—Yellow-green: 144C.
*Berry firmness*.—Medium.
*Particular flavor*.—Neutral.
*Bloom* (*cuticular wax*).—Medium.
*Berry separation from pedicel*.—Medium to easy.
*Skin color* (*without bloom*).—Yellow-green: 145C.
*Flesh color*.—Green-white: 157C.

Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine as herein illustrated and described.

* * * * *

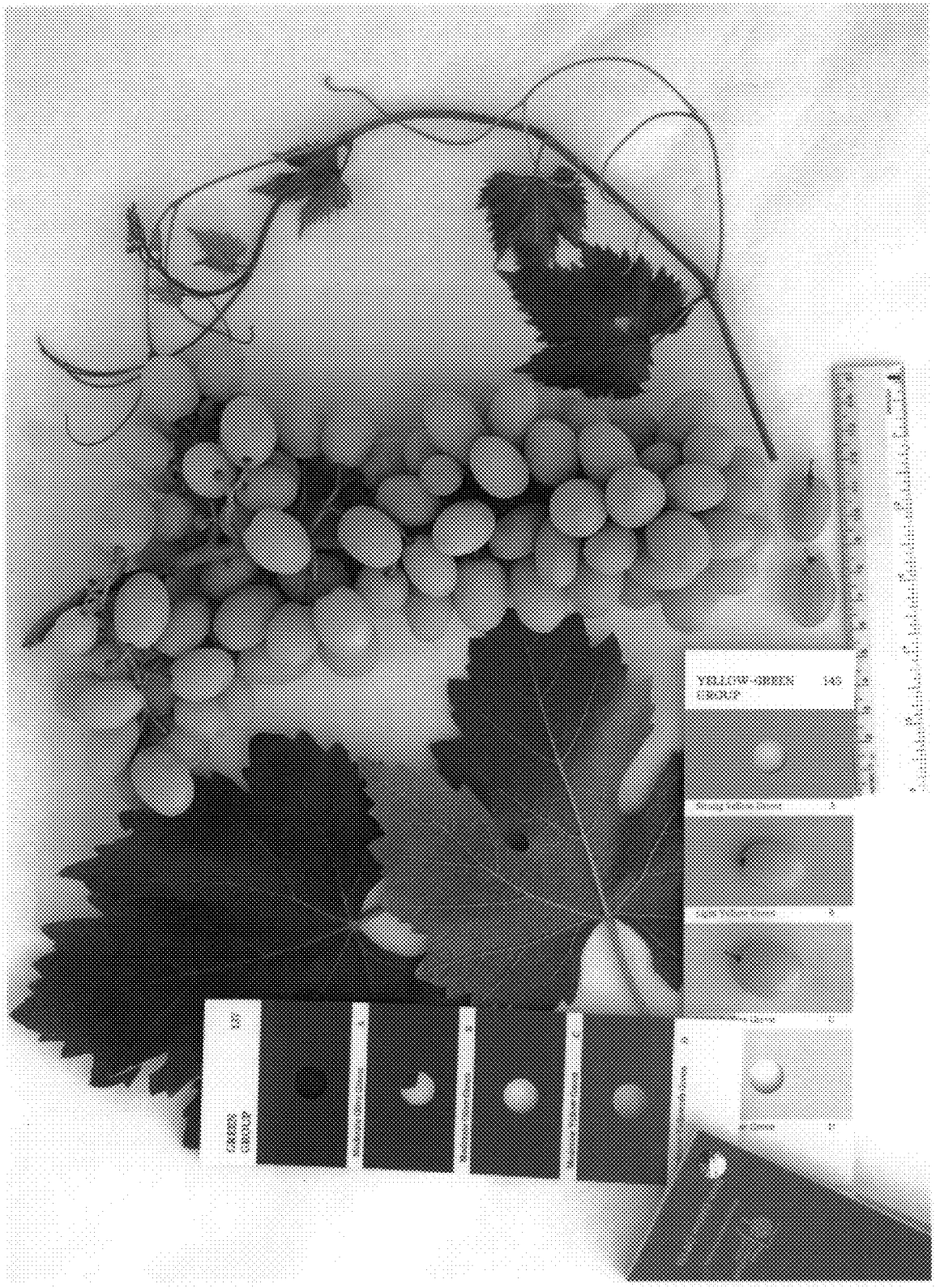
YELLOW-GREEN
GROUP
145
GREEN
GROUP
138